United States Patent [19]

Andresen

[11] Patent Number: 5,327,897
[45] Date of Patent: Jul. 12, 1994

[54] MULTIFUNCTION COLLECTING DEVICE FOR BODY FLUIDS

[75] Inventor: John A. Andresen, New Canaan, Conn.

[73] Assignee: Microbyx Corp., New Canaan, Conn.

[21] Appl. No.: 47,583

[22] Filed: Apr. 13, 1993

Related U.S. Application Data

[63] Continuation of Ser. No. 818,637, Jan. 6, 1992, Pat. No. 5,247,941.

[51] Int. Cl.⁵ .................. A61B 5/14; A61B 10/00; A61F 13/20
[52] U.S. Cl. ..................... 128/762; 128/769; 604/11; 604/54; 604/55; 604/328; 604/904
[58] Field of Search ............ 604/11, 54, 55, 285, 604/286, 327, 328, 330, 904; 128/637, 762, 769

[56] References Cited

U.S. PATENT DOCUMENTS

| | | | |
|---|---|---|---|
| 3,559,646 | 2/1971 | Mullar | 604/904 X |
| 3,867,924 | 2/1975 | Bucalo | 604/330 X |
| 3,924,607 | 12/1975 | Bucalo | 128/762 |
| 3,934,575 | 1/1976 | Bucalo | 128/762 |
| 3,958,561 | 5/1976 | Bucalo | 128/769 X |
| 3,998,211 | 12/1976 | Bucalo | 128/769 |
| 4,036,214 | 7/1977 | Bucalo | 604/328 X |
| 4,172,446 | 10/1979 | Bucalo | 128/769 |
| 4,186,730 | 2/1980 | Bucalo | 128/769 |
| 4,232,673 | 11/1980 | Bucalo | 604/904 X |
| 4,351,338 | 9/1982 | Langlois et al. | 604/55 X |
| 5,002,540 | 3/1991 | Brodman et al. | 604/55 X |

Primary Examiner—Randall L. Green
Assistant Examiner—Mary Beth Jones
Attorney, Agent, or Firm—Steinberg, Raskin & Davidson

[57] ABSTRACT

Methods and devices for collecting at least two separate samples of a body fluid (e.g., blood) simultaneously. The device is introduced into a body of a living being whose blood is to be analyzed at a preexisting accessible cavity of the body which at least temporarily contains blood of the living being. The device has an interior having first and second hollow retaining compartments capable of receiving and holding the blood which is present in the cavity when the entire device is introduced into and remains wholly within the cavity. After the device is removed from the body cavity, blood is removed from the first and second hollow retaining compartments, such that the blood can be simultaneously separately collected and prepared for subsequent separate and different analyses. The first and second hollow retaining compartments are adapted to collect blood having similar characteristics. In a preferred embodiment, the first and second retaining compartments each contain an absorbent medium such as a sponge. In a further preferred embodiment, the first and second retaining compartments further include an additive selected from the group consisting of a fixative, a preservative, nutrients, red cell stabilizers, an antibacterial, a germicide, an agglutinin, a surfactant, a detergent, an antibiotic, an additive to prevent hemolysis, and monoclonal antibodies, the additive within the first hollow retaining compartment being different from the additive within the second retaining compartment.

4 Claims, 2 Drawing Sheets

MULTIFUNCTION COLLECTING DEVICE FOR BODY FLUIDS

This is a continuation of application Ser. No. 07/818,637 filed Jan. 6, 1992 now U.S. Pat. No. 5,247,941.

BACKGROUND OF THE INVENTION

The present invention relates to methods and devices for collecting body fluids such as blood so that the fluid can thereafter be subjected to two or more separate analyses.

It is well known that in order to test the condition of a living being such as a human being or other animal, some of the blood is removed from the living being and is analyzed in a number of different ways. In many currently used methods, this blood is removed from the living being by undesirable methods. For example, it is known to prick the tip of a finger, an earlobe, or the like, and in addition, it is known to extract blood from an artery with a suitable syringe. These known procedures are highly disadvantageous since an essential part thereof involves wounding the body, creating pain and a certain amount of trauma and requiring not only operations under conditions of high standards of hygiene and sterility to avoid infection but also unavoidable discomfort which follows during healing of the wound required for extraction of blood.

Significant improvement for collecting body fluids are disclosed, for example, in U.S. Pat. Nos. 4,232,673, 4,036,214, 4,317,454, 3,958,561 and 3,867,924 (Re. 29,061), all of which are hereby incorporated by reference. In these patents, a device which is capable of receiving and holding blood is introduced into the interior of a body cavity where blood is present, and after the device remains in the body cavity for a sufficient amount of time to receive a suitable amount of blood, the device is removed and the blood removed therewith is tested. Such devices may be incorporated into a tampon introduced into the vagina for collecting blood during the menstrual cycle.

SUMMARY OF THE INVENTION

It is an object of the present invention to provide a method and device which may be used for collection of a body fluid such as blood such that the body fluid may be easily separated into two or more separate samples and subjected to two or more different analyses.

It is a further object of the invention to provide a method and device according to which it is possible to extract and analyze blood without wounding the living being in any way (and thereby without requiring any healing procedures in connection therewith) for the purpose of obtaining two or more separate blood samples for different analyses.

It is a further object of the present invention to provide a device which can be used at any part of the body of a living creature where blood is present for the purpose of extracting two or more separate samples of this blood so that it can then be subjected to different analyses.

It is a further object of the present invention to provide a method and device of the above type which creates no discomfort whatsoever, thus rendering it possible to achieve painless blood extraction without any possibility of infection in connection with the extraction of the blood for two or more different analyses.

According to the present invention, a device which is capable of receiving and holding blood is introduced into the interior of a cavity of a body of a living creature, this cavity being one in which blood is in any event present. The device is removed from the cavity after the device has remained therein for a period of time sufficient to receive and hold blood, which is thus removed with the device. The device is then separated into separate compartments such that the blood in each of these compartments can then be subjected to different analyses.

The above device of the invention includes an outer holder which is formed with an entrance means through which blood can flow into the interior of the holder, and within the interior of the holder are two or more separate compartments capable of retaining and holding the blood. According to a particular feature of the invention, this device may be incorporated into a tampon inserted into the vagina during the menstrual cycle.

In certain embodiments of the present invention, each of the compartments may be impregnated with or contain a different substance for facilitating the later analysis of the blood contained therein. Such substances include, for example, a fixative, a preservative, nutrients, red cell stabilizers, an antibacterial, a germicide, an agglutinin (for clotting the red cells), a surfactant, a detergent, an additive to prevent hemolysis (such as dextran), an antibiotic (to kill certain microorganisms collected in a body fluid sample in which there is no particular interest), and monoclonal antibodies (e.g., to detect the HIV virus), etc. The term "microorganisms" for purposes of the present invention is deemed to include bacteria, fungi, and viruses.

In a preferred embodiment of the present invention, the device is a tampon which is assembled to collect menses. After removal from the vagina, the device is separable into two or more parts having separate compartments, each with a sponge or absorbent containing the menses. The parts may then be placed, for example, in a preservative and/or fixative solution contained in vials, which are then sent to a laboratory for analysis by standard procedures, or by an automated analysis system.

In a preferred embodiment, the analysis is conducted by means of the automated analysis system disclosed in U.S. Pat. No. 4,066,359, hereby incorporated by reference. The device of the present invention provides a means by which analysis of the menses may be accomplished simultaneously to detect vaginal cancer, sexually transmitted diseases, hepatitis B, AIDS, and other possible disease indications.

BRIEF DESCRIPTION OF THE DRAWINGS

The following drawings are illustrative of embodiments of the invention and are not meant to limit the scope of the invention as encompassed by the claims.

DETAILED DESCRIPTION

In accordance with the invention, any internal body cavity where blood is encountered may be used for the purposes of the present invention. This cavity may be the vagina or any other cavity such as a sinus passage, the interior of the mouth, the passage leading from the ear, the anal canal, or the like. Within this cavity there is inserted in accordance with the invention a device which is small enough to be comfortably received in the body cavity and retained therein while at the same time being large enough to receive and hold an amount of blood sufficient for subsequent analysis.

Figure 1:
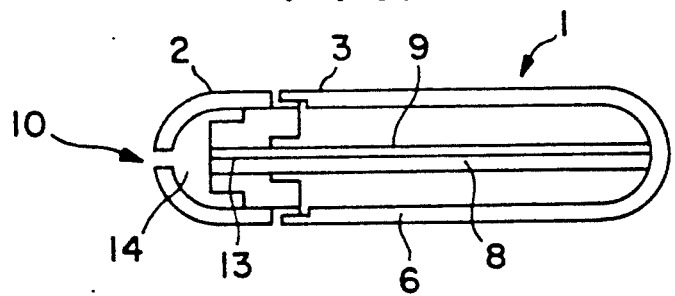
FIG. 1 is a schematic section elevation of one possible embodiment of an apparatus for carrying out a method according to the invention.

Turning now to the embodiment depicted in FIG. 1, the device 1 comprises a cap portion 2 and a body portion 3. The wall 6 can be made of any material which is compatible with the human body such as any one of a number of different metals and any one of a number of different plastics which will not soften or melt at body temperature. Thus, it is possible to use for this purpose polyethylene, polypropylene, polyvinylchloride, polystyrene, etc.

In the embodiment shown in FIG. 1, a first hollow retaining compartment 8 is located within the device 1, which retaining means is capable of retaining the blood which flows into the interior of the holder 1 through entrance 10. A second separate hollow retaining compartment 9 is also located within the device 1. Retaining compartment 9 is structurally identical to retaining compartment 8 in the embodiment of FIG. 1. However, the separate retaining compartments 8 and 9 may be structurally different from each other if desired. Retaining compartments 8 and 9 are separated by wall 13 in FIG. 1.

Retaining compartments 8 and 9 in the embodiment depicted in FIG. 1 have the form of a elongated tube divided into two sections which is open at one end so as to be provided with an entrance means 10 through which the blood may flow freely into the interior of the device.

Figure 2:
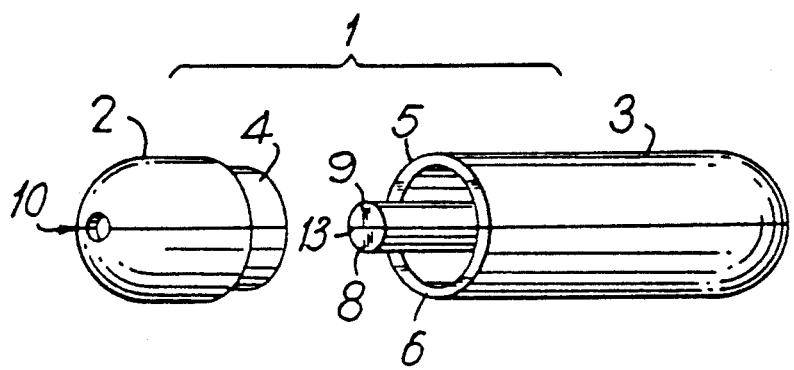
FIG. 2 is a fragmentary illustration of the embodiment of FIG. 1.

In FIG. 2, it is seen that in the embodiment shown in FIG. 1, the cap portion 2 can be separated from the body portion 3 of the device 1. The cap portion 2 and the body portion 3 include mating flanges 4,5 where they are Joined together and where they are releasably retained in connection with each other by friction or by the use of a suitable adhesive if desired. Alternatively, the cap portion 2 can be screwed onto the body portion 3.

Figure 3:
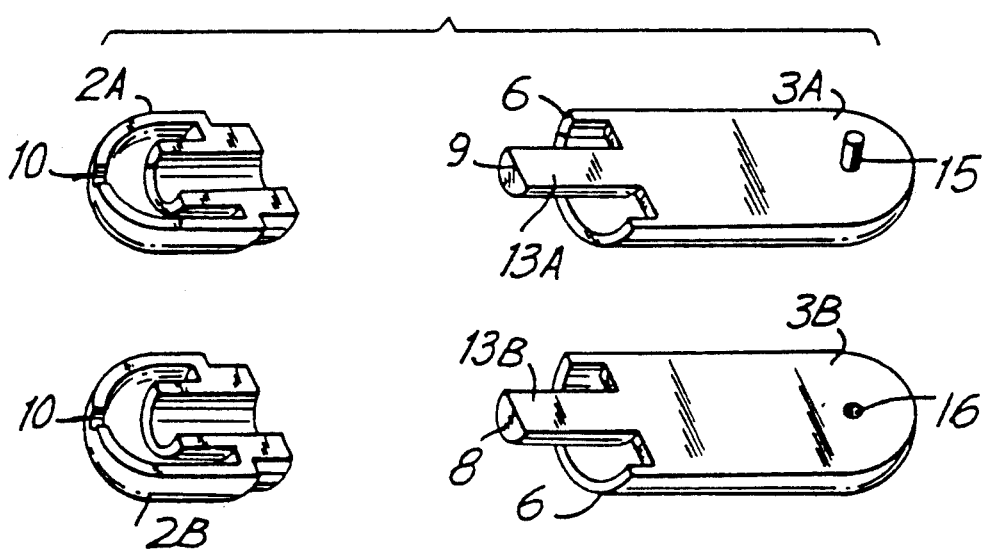
FIG. 3 is a longitudinal sectional illustration of a section of the embodiment of FIG. 1 after the embodiment of FIG. 1 has been separated into separate compartments.

FIG. 3 is a longitudinal sectional illustration of a section of the embodiment of FIG. 1 after the embodiment of FIG. 1 has been separated into separate compartments and the blood which has been collected in separate compartments 8 and 9 is to be tested. As can be seen, cap portion 2 of the device separates into cap halves 2A and 2B, while body portion 3 separates into body halves 3A (which in this embodiment includes compartment 9) and 3B (which in this embodiment includes compartment 8). In the embodiment depicted in FIG. 3, separating wall 13 comprises a first wall part 13A and a second wall part 13B.

Body halves 3A and 3B are shown in FIG. 3 as being connectable by a projection 15 on section 3A, which fits into recess 16 on section 3B. Cap halves 2A and 2B can be likewise connected. Alternatively, any manner of connecting cap halves 2A and 2B, and body halves 3A and 3B, may be used.

Figure 4:
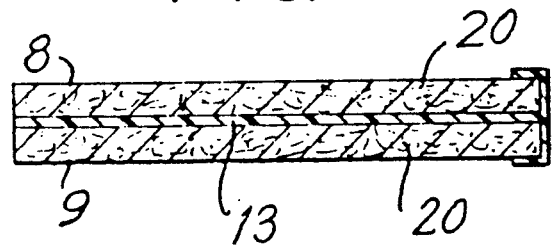
FIG. 4 is a cross-sectional view of the retaining compartments of the embodiment of FIG. 1 showing the retaining means.

As shown in FIG. 4, the retaining compartments 8 and 9 preferably include in their interior a retaining means 20 which is also compatible with the interior of a human being, in this embodiment a sponge. The retaining means may be in the form of a compressed body of filamentary material such as cotton wadding, or a sponge.

Instead of a sponge, another absorbent material may be used as the retaining means. Likewise, instead of cotton wadding, it is possible to use a filamentary materials such as a compressed body of fine gold wire, since gold is known to be compatible with human beings. Even though a metallic wire filament which does not have absorbent properties may be utilized, the surface tension in the blood will cause the blood to be retained at the interstices formed in the interior of the body of compressed wire, and in addition, it is to be noted that it is possible to use combinations of filamentary material such as gold wire and cotton, for example. Other filamentary materials may be used to form the retaining means, such as, for example, fine monofilaments of plastic. Thus, any plastic compatible with the human body such as nylon, polyesters, and the like, is readily available in fine filamentary form in which it can be compressed into a body held in the device 1 and forming the separate retaining compartments 8 and 9.

Figure 5:
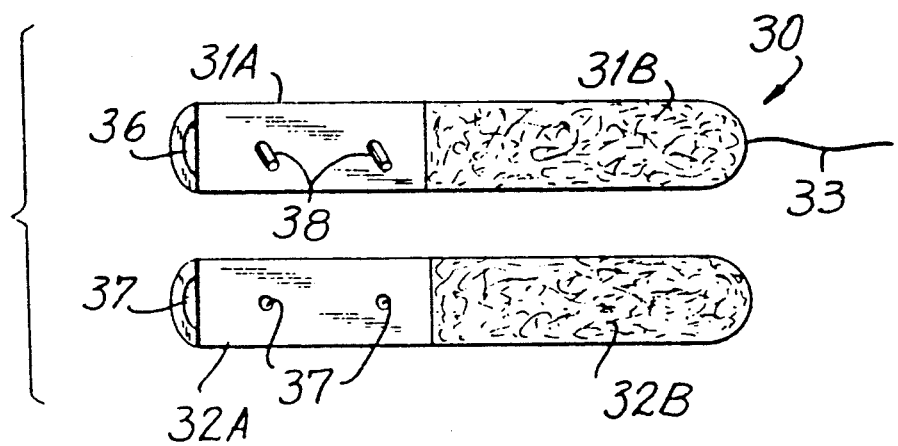
FIG. 5 is a schematic illustration of another possible embodiment of an apparatus for carrying out a method according to the invention.

The device of the invention need not take the specific form shown in FIGS. 1-3. For example, FIG. 5 shows another embodiment of the device of the present invention, which may be made of any of the materials used for the embodiment shown in FIGS. 1-3. In this embodiment, the device 30 comprises two body halves 31 and 32, which are connected to each other during use via protrusions 38 and corresponding recesses 39. Each body halve 31, 32 is further divided into upper body halves 31A, 32A and lower body halves 31B and 32B, respectively. The upper body halves each have a retaining compartment 36, 37 which includes a retaining means as described above for FIGS. 1-3. The lower body halves 31B, 32B, attached to the upper body halves 31A, 32A in any manner known in the art, comprises tampons, as are conventionally used by female human being during the menstrual cycle. Thus, tampon sections 31B, 32B are introduced into the vagina during the menstrual cycle, and a string 33 extends from at least one of tampon sections 31B, 32B such that the device 30 can be removed from the body cavity.

Figure 6:
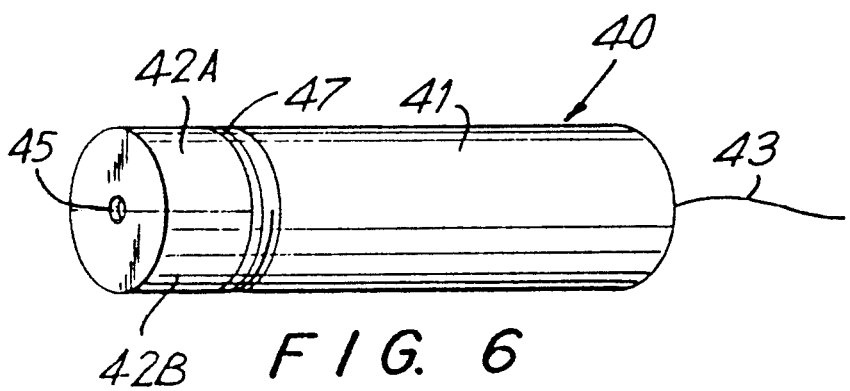
FIG. 6 is yet another schematic illustration of a possible embodiment of an apparatus for carrying out a method according to the invention.

In the embodiment depicted in FIG. 6, the device 40 comprises a lower body portion 41 which comprises a tampon. The tampon is attached to an upper cap portion 42 via a screw arrangement 47. In FIG. 6, the upper cap portion 42 is shown partially unscrewed from the lower body portion 41.

The upper cap portion 42 of the embodiment depicted in FIG. 6 is divided into two detachable halves 42A and 42B. Each detachable half 42A, 42B includes a retaining compartment (not shown) having a retaining means (not shown) as described above. The body fluid, e.g. blood, enters the retaining compartments via entrance 45. A string 33 extends from the lower body portion 41 comprising a tampon, such that the device 30 can be removed.

In practicing the method of the invention, the device of the invention is inserted into a body cavity where blood will be encountered. Thus, as pointed out above, the tampon is introduced into the vagina during the menstrual cycle. However, it is possible to introduce any of the devices of FIGS. 1-6 into a cavity such as the anal canal in an individual who is suffering from hemorrhoids, for example. Also, where there is bleeding of the gums in the mouth of a human being or bleeding in the mouth from any source, it is possible to situate the device in the interior of the mouth, wedged between the gums and lips, for example. It is possible to introduce the device of the invention into the ear where bleeding is encountered in the ear. It is also possible to introduce the device into a nostril where bleeding is encountered or into a sinus where bleeding is encountered. Thus, wherever blood is encountered in a body cavity, either as the result of natural functioning of a healthy human being, as would be the case with the tampon, or as the result of an illness, and operation, or the like in any body cavity, it is possible to use the device of the invention. Thus, in accordance with the method of the invention the device of the invention is inserted in to the body cavity and is permitted to remain at the body cavity for a period of time which is sufficient to enable blood to flow freely into the interior of the holder of the device and to be retained by the retaining means therein. Thereafter, the device is removed from the interior of the body cavity and the blood in the device can be tested in any conventional manner. For example, the two sections 8 and 9 of device 1 of FIG. 1 are removed from each other and the retaining means may be used to smear slides which can be examined under the microscope and it can be compressed in any suitable way so as to cause the liquid blood to be compressed out of the retaining means and received in any suitable container to which additional materials are added for testing purposes, as is well known. For example, the blood which is squeezed from the retaining means may be received in a test tube which has in it a known reagent, and such test tubes are then capable of being placed in blood analyzing machines such as well known machines which optically analyze the blood.

For purposes of the present invention, the term "accessible" as used with reference to a cavity of the body is intended to mean a body cavity to which access may be had without requiring any procedures such as piercing a part of the body with a needle, for example. Thus, an "accessible cavity" is intended to mean a body cavity the interior of which is accessible because of the nature of the cavity, such cavities being, for example, the vagina, the mouth, the ear, the nose, the rectum, and the like, all of which are accessible without puncturing or otherwise wounding the body and all of which may at times have internal bleeding which provides a source of blood which may be used with the present invention. In addition, however, the term "accessible" is intended to cover body cavities which become accessible for reasons other than collection of blood. For example, any interior part of the body which becomes accessible due to wounding of the body by accident or due to surgical procedures are also considered to be "accessible" in the sense called for by the claims inasmuch as such cavities also are sources of blood which can be collected and tested although these cavities do not become accessible for the purpose of obtaining samples of blood for testing purposes.

It is apparent, therefore, that with the present invention, in order to test the blood of an individual, it is not necessary to wound the individual, and instead, it becomes possible to utilize blood which is in any event present at a body cavity for the purpose of blood testing.

An important aspect of the present invention is that, by virtue of the at least two separate compartments provided, separate samples of body fluid may be removed for different analyses simultaneously and without wounding the subject.

In one preferred embodiment of the present invention, a suitable additive is included in the retaining compartment as a pre-treatment for the body fluid prior to analysis. Such additives may be included in the retaining compartment by any means known in the art, including but not limited to being coated on the retaining means, or being embedded in the inner walls of the retaining compartment.

In one preferred embodiment, a blood preservative such as citric acid is incorporated into the retaining means.

The additive which may be contained in the retaining compartment may also comprise a suitable nutrient for suspected microorganisms, and it also may contain certain antibiotics for making certain that microorganisms in which there is no interest are killed so as not to disturb the viewing of the suspected microorganisms. For example, when it is suspected that certain microorganisms are present in the body fluids, the device when inserted into the desired accessible cavity will contact body fluids containing the microorganisms. These microorganisms will flow along with the body fluid into the retaining compartment and into the retaining means, e.g., a sponge. This sponge will absorb the liquid containing the microorganisms.

The device of the present invention may be permitted to remain in the body cavity for as long as desired, e.g., so as to assure growth of microorganisms directly in the body cavity.

After the desired time, the entire device can be removed from the body cavity in any suitable way and inspected to determine the presence or absence of microorganisms. This inspection may be enhanced by opening the retaining compartment and introducing into the sponge a suitable dye by way of a suitable syringe, for example, so that with this dye, the visibility of suspected microorganisms is greatly enhanced.

In another embodiment of the present invention, monoclonal antibodies may be included in the retaining compartment, e.g. for use in the detection of the HIV virus, etc. Thus, by virtue of the present invention, the separate compartments may contain different monoclonal antibodies for the simultaneous detection of different antigens in the body.

However, it is to be understood that, if desired, no nutrients or antibiotics need be located in the retaining compartment, since the absorbed fluids can be treated subsequent to the removal of the device from the body cavity if so desired.

It is preferred, however, to include the desired additives in the retaining compartments because, for example, it is desirable to grow the microorganisms in the body cavity because the conditions prevailing therein are ideal for this purpose.

The examples provided above are not meant to be exclusive. Many other variations of the present invention would be obvious to those skilled in the art, and are contemplated to be within the scope of the appended claims.

I claim:

1. A device made of a biocompatible material for collecting a body fluid in a body cavity, comprising means for inserting said device into said body cavity, said means comprising,
   an exterior portion,
   an interior portion said device further comprising, said interior portion comprising,
   a single passage connecting said interior portion to said exterior portion of said device, the body fluid flowing through said passage into said interior portion from said exterior portion,
   a first hollow retaining compartment for collecting a sample of body fluid when the device is situated in a body cavity, and
   a second hollow retaining compartment for collecting a second sample of body fluid when the device is situated in the body cavity, said second hollow retaining compartment being structured and arranged to collect body fluid having similar characteristics as that collected in said first hollow retaining compartment, said single passage connecting said first and second hollow retaining compartments to said exterior portion of said device, and
   retaining means situated in each of said first and second retaining compartments, at least a portion of the body fluid passed through said passage and into said interior portion and thereafter collected in said first and second retaining compartments being retained on said retaining means, the body fluid being simultaneously passed from said interior portion and separately collected in both of said first and second retaining compartments and prepared for subsequent separate and different analyses of the collected body fluid from each of said first and second retaining compartments.

2. The device of claim 1, further comprising a first additive included in said first retaining compartment as a pre-treatment for the collected body fluid prior to removal of said device from the body cavity, and a second additive included in said second retaining compartment as a pre-treatment for the body fluid collected in said second retaining compartment prior to removal of said device from the body cavity, said second additive being different from said first additive.

3. In a method for collecting and analyzing the blood of a living being, the steps of providing a device having an interior having first and second hollow retaining compartments each having retaining means therein capable of receiving and holding blood which is present in the cavity when the entire device is introduced into and remains wholly within the cavity, said interior having a single passage structured and arranged to pass blood from the cavity through said passage and simultaneously to both of said first and second hollow retaining compartment,
   introducing into a body of a living being whose blood is to be analyzed, at a preexisting accessible cavity of the body which at least temporarily contains blood of the living being, said device being introduced in the cavity at a time which will assure presence of the device in the cavity when blood is present therein,
   removing the device from the body cavity after the device has remained therein for a period of time sufficient to receive and hold blood of the living being, so that blood is removed with the device, said second hollow retaining compartment being adapted to collect blood having similar characteristics as that collected in said first hollow retaining compartment,
   providing said retaining means within said first and second hollow retaining compartments prior to introduction of the device into the body cavity with an additive selected from the group consisting of a fixative, a preservative, nutrients, red cell stabilizers, an antibacterial, a germicide, an agglutinin, a surfactant, a detergent, an antibiotic, an additive to prevent hemolysis, and monoclonal antibodies, the additive within said first hollow retaining compartments being different than the additive within said second hollow retaining compartment, subjecting at least part of the blood contained within said first hollow retaining compartment to a first analysis, and
   subjecting at least part of the blood contained within said second hollow retaining compartment to a second analysis different than said first analysis.

4. The method of claim 3, further comprising providing a portion of said device as a tampon means.

* * * * *